Figure 1A:
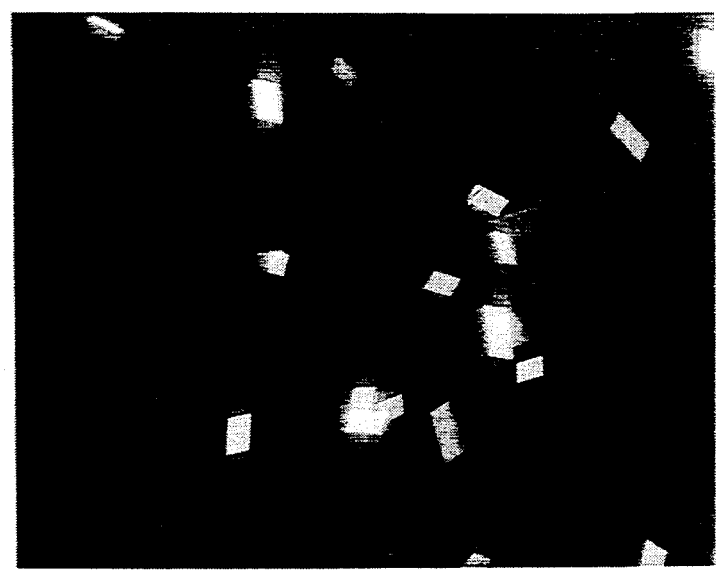

United States Patent [19]

Krishnamurthy et al.

[11] Patent Number: 5,426,021

[45] Date of Patent: Jun. 20, 1995

[54] LIQUID OR LOW MELTING BIS-PHENOL STABILIZERS FOR YELLOW IMAGE DYE STABILIZATION IN EKTACOLOR PAPER

[76] Inventors: Sundaram Krishnamurthy; Rakesh Jain; Paul P. Spara; Thomas A. Rosiek, all of Eastman Kodak Company, Rochester, N.Y. 14650

[21] Appl. No.: 86,977

[22] Filed: Jul. 2, 1993

[51] Int. Cl.$^6$ .................. G03C 7/392; G03C 7/36
[52] U.S. Cl. .................. 430/551; 430/546; 430/556; 430/557
[58] Field of Search .............. 430/551, 546, 617, 610, 430/611, 607, 556, 557

[56] References Cited

U.S. PATENT DOCUMENTS

| | | | |
|---|---|---|---|
| 3,414,639 | 12/1968 | Hodan et al. | 260/953 |
| 3,755,069 | 8/1973 | Crawford et al. | 162/135 |
| 4,365,032 | 12/1982 | Yosizato et al. | 524/99 |
| 4,526,864 | 7/1985 | Takada et al. | 430/551 |
| 4,748,100 | 5/1988 | Umemoto et al. | 430/505 |
| 4,782,011 | 11/1988 | Goddard et al. | 430/551 |
| 4,906,555 | 3/1990 | Hirose et al. | 430/505 |
| 5,021,333 | 6/1991 | Leyshon et al. | 430/551 |
| 5,059,515 | 10/1991 | Leppard | 430/551 |
| 5,087,768 | 2/1992 | Nonn | 568/730 |
| 5,194,348 | 3/1993 | Morigaki et al. | 430/17 |
| 5,202,458 | 4/1993 | Leppard | 560/67 |

FOREIGN PATENT DOCUMENTS

| | | |
|---|---|---|
| 0246766 | 4/1987 | European Pat. Off. . |
| 0349382 | 1/1990 | European Pat. Off. . |
| 0520726 | 6/1992 | European Pat. Off. . |
| 0500323 | 8/1992 | European Pat. Off. . |
| 0508398 | 10/1992 | European Pat. Off. . |
| 2948969 | 6/1980 | Germany . |
| 2178241 | 8/1987 | Japan ................. 430/551 |
| 4340960 | 11/1987 | Japan . |
| 1-289952 | 5/1988 | Japan . |
| 1137258 | 5/1989 | Japan . |
| 1-152456 | 6/1989 | Japan . |
| 1144048 | 6/1989 | Japan . |

OTHER PUBLICATIONS

"The Stabilization of Dye Images Produced In Photographic Silver Halide Materials" Research Disclosure, Nov., 1992; pp. 853–855.

*Primary Examiner*—Lee C. Wright

[57] ABSTRACT

A photographic element containing a silver halide emulsion layer having associated therewith, a dye-forming coupler and a dye stabilizer which has a melting point of less than 150° C. (and preferably less than 100° C.) and is of the formula:

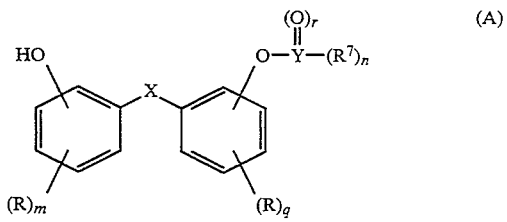

wherein R, m, q, X, Y, r, and $(R^7)_n$ are defined in the specification.

The element particularly contains a coupler which forms a yellow dye upon reaction with oxidized developer. A method of making stabilizers of the above type using particular solvents and a non-aqueous workup, is also provided.

14 Claims, 3 Drawing Sheets

LIQUID OR LOW MELTING BIS-PHENOL STABILIZERS FOR YELLOW IMAGE DYE STABILIZATION IN EKTACOLOR PAPER

FIELD OF THE INVENTION

This invention relates to silver halide photographic elements and particularly to the stabilization of dye images produced in such elements.

BACKGROUND OF THE INVENTION

Color photographic elements typically contain several records each with silver halide sensitized to a different region of the visible light spectrum. Generally, one record is sensitized to red light, another green light and another, blue light. Each of the foregoing records also contains a color coupler which reacts with oxidized developer during processing of the element, to produce a dye in a pattern corresponding to the image to which the element was exposed. In a typical element the red, green and blue sensitive records respectively contain a cyan dye forming coupler, a magenta dye forming coupler and a yellow dye forming coupler. The color couplers are typically provided in the form of droplets of a coupler solution in an organic solvent, which droplets are dispersed in the gel medium (typically gelatin) of the element.

The dyes that are formed by any color coupler during processing have a tendency to fade over time particularly as a result of exposure to light. As all three image dyes of a typical color element fade, this results in overall fading of the image over time. In addition, since the three image dyes may not fade at the same rate, an apparent change in image color also results. Stabilizers are classes of compounds which reduce the foregoing image dye fading problem. Known stabilizers include phenols, bis-phenols, blocked phenols, blocked bis-phenols, metal complexes and other compounds used in conjunction with many different color couplers. Photographic elements containing the foregoing color coupler and stabilizer combinations are described, for example, in EP 0 298 321; EP 0 231 832; EP 0 161 577; EP 0 218 266; EP 0 246 766; U.S. Pat. No. 3,043,697; U.S. Pat. No. 3,700,455; Kokai JP 62043-641, JP 01137-258, JP 01144-048; U.S. Pat. No. 4,782,011 and U.S. Pat. No. 4,748,100.

However, not all of the above types of stabilizers are equally effective at stabilizing all image-dyes. It is desirable then, to provide photographic elements which incorporate stabilizers which are particularly effective at stabilizing the image dyes formed as a result of processing the element.

SUMMARY OF THE INVENTION

The present inventors have found that one of the difficulties with many types of blocked bis-phenol type stabilizers, is that they tend to crystallize in the coupler dispersion environment which results in reduced effectiveness. It has been found that bis-phenol stabilizers of certain structures and with relatively low melting points, result in dispersions which do not crystallize as readily as when other stabilizers are used. This results in the ability to employ broader concentration ranges of stabilizers of the present invention in photographic dispersions, without crystallization. Further, stabilizers of the present invention provide particularly effective stabilization. In addition, ester type stabilizers of the present invention can be readily synthesized in higher yields in shorter reaction times versus bis-phenol type stabilizers of the ether type. The present invention therefore provides a photographic element comprising a silver halide emulsion layer having associated therewith, a dye-forming coupler and a dye stabilizer which has a melting point of less than 150° C. (and preferably less than 100° C.) and is of the formula (A):

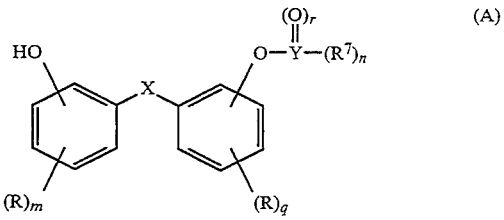

wherein:
each R independently represents an alkyl, alkenyl, cycloalkyl or aryl group, or in combination with the benzene ring to which it is attached represents the atoms necessary to complete a fused ring system, any of the foregoing being substituted or unsubstituted;
m and q independently represent an integer of 0 to 3;
x represents a linking group or a single bond;
Y represents C, S or P;
r is 1 when Y is C or P, and is 1 or 2 when Y is S; and
$(R^7)_n$ is $R^7$ when Y is C or S (that is, n=1), or is $(OR^8)_2$ when Y is P, in which $R^7$ and $R^8$ independently represent a substituted or unsubstituted aliphatic or aromatic group.

The present invention also provides a method of synthesizing stabilizers of the above type, which method comprises reacting the corresponding bisphenol compound with an acylating, aroylating, sulfonylating, or phosphorylating agent in an a carboxylic acid ester solvent. A method of recovering the stabilizer produced by a reaction of the foregoing type (but not necessarily in a carboxylic acid ester solvent), is also provided which comprises filtering the reaction mixture and recovering the stabilizer from the filtrate (typically by solvent removal or crystallization of stabilizer) without adding water to the reaction mixture in order to recover the stabilizer (that is, the workup is non-aqueous).

DRAWINGS

Figure 1B:
Figure 1C:
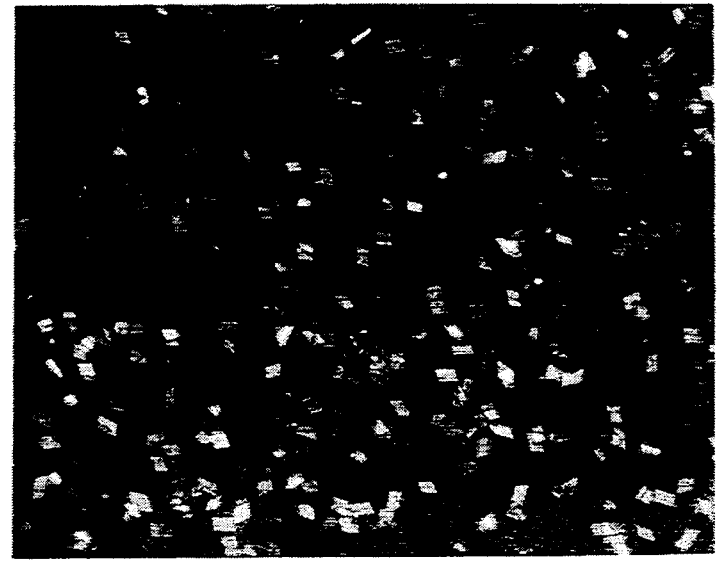
Figure 1D:
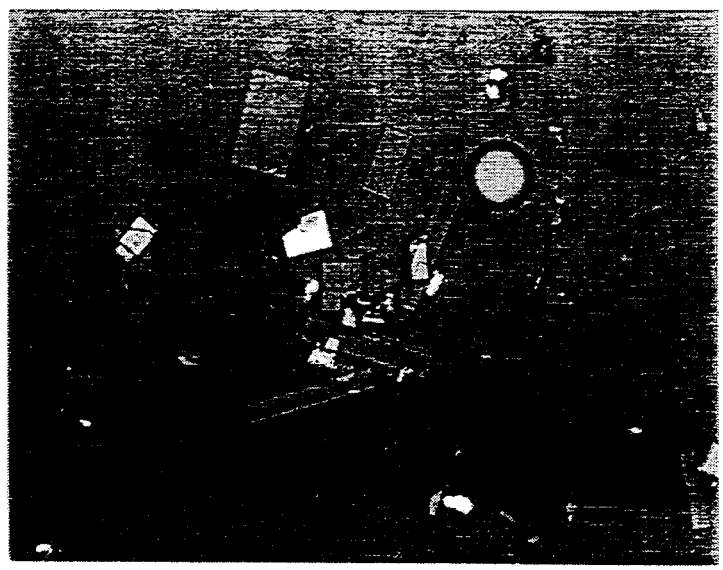
Figure 1E:
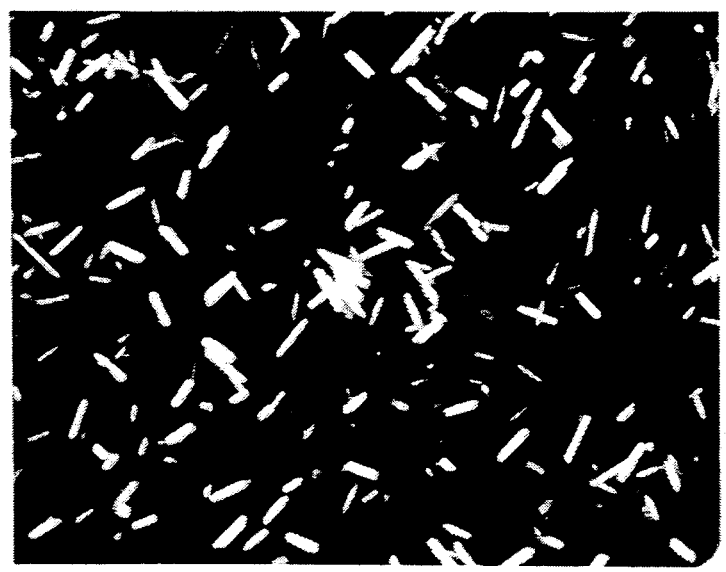
Figure 1F:
Figure 1G:
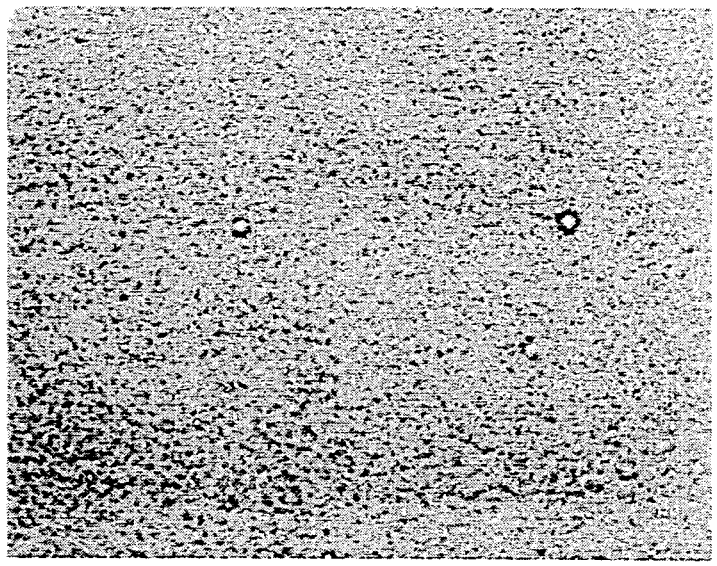
Figure 1H:
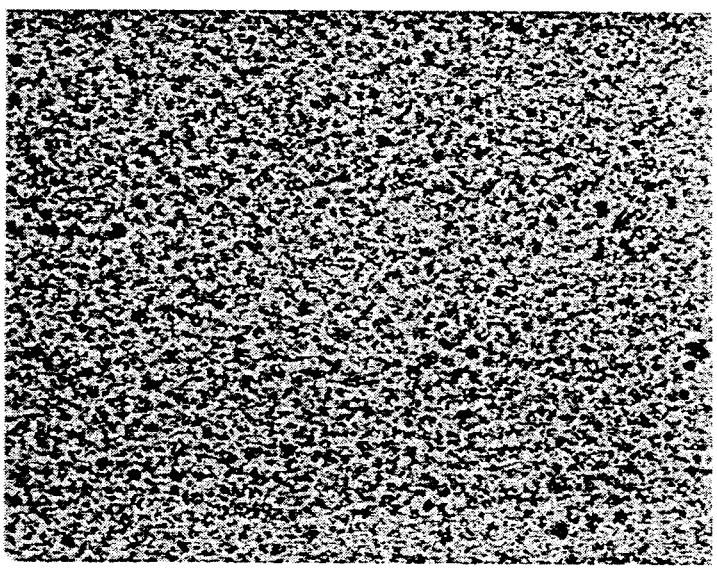
Figure 1I:
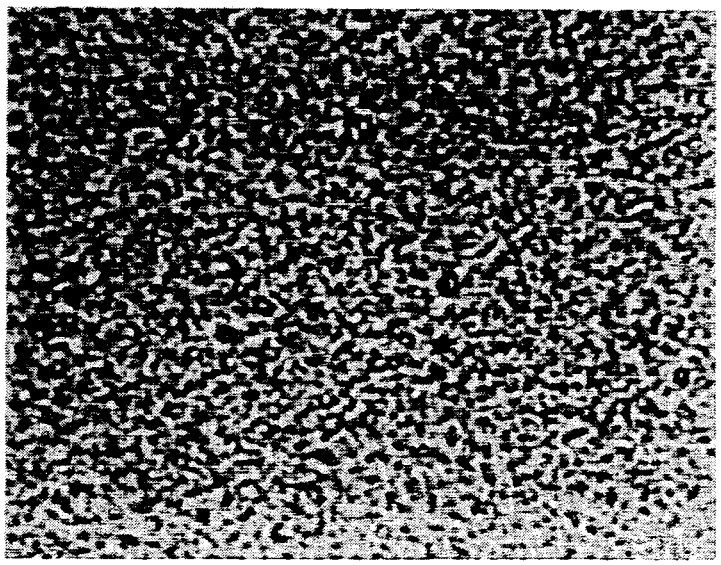

FIG. 1 shows photomicrographs (all at 98×magnification) of dispersions prepared and tested in accordance with Example 1 with the respective stabilizer, formulation method and time as follows: (a) SC-1, A, I, 24 h; (b) SC-1, B, I, 24 h; (c) SC-1, C, I, 24 h; (d) SC-2, B, I, 96 h; (e) SC-2, B, II, 24 h; (f) SC-3, B, I, 96 h; g) S-5, C, I, 96 h; h) S-9, B, I, 24 h; i) S-2, C, I, 24 h.

EMBODIMENTS OF THE INVENTION

By "associated" in the above description, is meant that the coupler is in the silver halide emulsion layer or in an adjacent location where, during processing, the coupler is capable of reacting with silver halide development products. Similarly, the stabilizer is in the or in an adjacent location where it is capable of having its effect on the dye formed by the coupler. Preferably both the coupler and stabilizer will be in the same layer as the silver halide emulsion layer. More preferably, the stabilizer will have been dissolved in the same solvent containing the coupler, and which solution is dispersed in the silver halide emulsion layer.

Groups which may be used for any of R in formula (A) may particularly include substituted or unsubstituted cyclohexyl or phenyl, but more preferably contain 1 to 4 C atoms. It is particularly preferred that R be a methyl or tert-butyl, preferably unsubstituted. As already mentioned, X is a single bond or a bivalent linking group. Such linking groups include: an alkylidene, for example, methyline, butylidene or 3,3,5-trimethyl-hexylidene, any of which may be substituted or unsubstituted; a heteroatom, for example, oxygen, sulfur, selenium, or tellurium; sulfonyl or phosphinyl.

Particularly, but not only, when Y is C (which implies r and n are both 1), $R^7$ may be a substituted or unsubstituted alkyl group, for example a $C_1$ (or $C_2$), to $C_{30}$ (or $C_5$-$C_{30}$) alkyl such as hexyl, butyl, n-pentyl, 2-methylbutyl, n-octyl, 2-ethylhexyl, n-decyl, 2-ethoxyethyl, 4-methoxybenzyl, or even a $C_5$-$C_{30}$ alkyl; a substituted or unsubstituted trialkylsilyl group each alkyl group being $C_1$-$C_{30}$; a substituted or unsubstituted cycloalkyl group, for example, 2-methylcyclohexyl group; a substituted or unsubstituted alkenyl or alkynyl group; a substituted aryl group, for example 4-dodecyloxyphenyl. When Y is P (which implies r=1 and n=2), each $R^8$ can be any of the same groups as $R^7$ but may particularly independently be a substituted or unsubstituted alkyl group, particularly having 1, 2, 3 or 4 C atoms. When Y is S (which implies r=1 or 2, and n=1), $R^8$ may particularly be a substituted or unsubstituted aryl group such as phenyl, or a substituted or unsubstituted alkyl group including $C_1$, $C_2$, $C_3$ or $C_4$ alkyl groups.

It will be appreciated that although the substituents may be chosen from types previously specified, the stabilizer should still have a melting point of less than 150° C. Preferably, the melting point of the stabilizer of formula (A) is less than 100° C. (or even 90° C.), and more preferably the melting point is between 30° C. to 100° C. (or 90° C.) or between 50° C. and 100° C. (or 90°).

A preferred stabilizer of the type of formula (A), is that represented by formula (B) below:

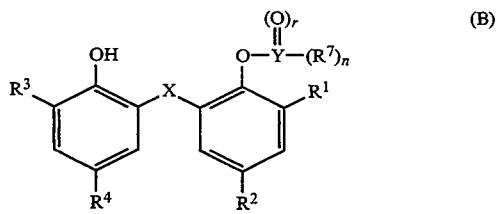

(B)

In formula (B), each of $R^1$, $R^2$, $R^3$ and $R^4$ independently represents an alkyl, alkenyl, cycloalkyl or aryl group, any of which may be substituted or unsubstituted. Preferably, $R^1$ and $R^3$ are the same, and $R^2$ and $R^4$ are also the same (but not necessarily the same as $R^1$ and $R^3$). $R^7$ in formula (B) may further preferably be a substituted or unsubstituted aliphatic group. X may further preferably represent —$CR^5R^6$— where $R^5$ and $R^6$ are the same and together represent hydrogen or a substituted or unsubstituted $C_1$ to $C_4$ alkyl. It is further particularly preferred that Y is C (and hence r=1 and n=1), such that the stabilizers are of formula (C) below:

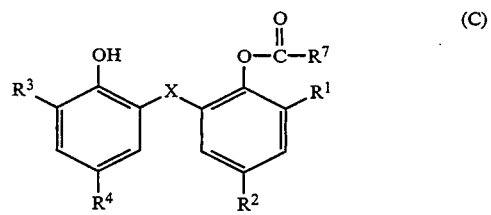

(C)

Even further preferably, X is $CH_2$ such that the stabilizers are of the formula (D) below:

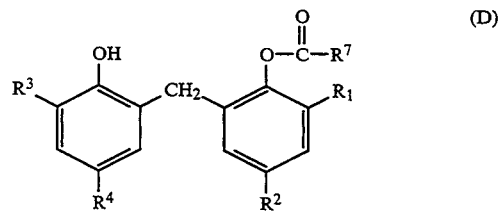

(D)

Instead of using stabilizers of formula (A), (B), (C) or (D), the equivalent type of ether stabilizers could be used. That is, the structural formulae would be the same as (A), (B), (C) and (D) except the carbonyl group is deleted such that $R^7$ is directly bonded to the —O— attached to the phenyl ring (referenced herein as formulae (A'), (B'), (C') and (D')). For example, formula (A') and (D') would be:

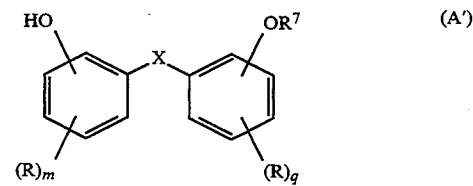

(A')

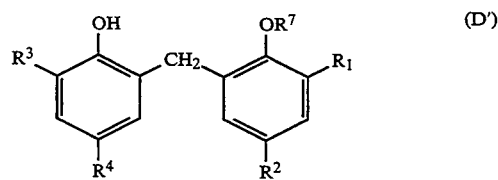

(D')

The substituents would all have the same limitations and preferences as outlined in connection with the corresponding structures (A), (B), (C) or (D). However, in the case of any of formulae (A'), (B'), (C') or (D') it is particularly desirable that $R^7$ would be a substituted or unsubstituted alkyl or alkenyl group not containing any aromatic substituents (and preferably of more than 4 C atoms), and $R^2$ and $R^4$ would be a substituted or unsubstituted alkyl or alkenyl group (this would, of course, exclude alkoxy groups), with t-butyl and methyl being particularly preferred. Further, $R^1$ and $R^3$ in such stabilizers may particularly be acyclic, with t-butyl being particularly preferred. Such stabilizers would also have a melting point of less than 150° C., and preferably the melting point of the stabilizer of formulae (A'), (B'), (C') or (D') is less than 100° C. (or even less than 90° C.), and more preferably the melting point is between 30° C. to 100° C. (or 90° C.) or between 50° C. and 100° C. (or 90° C.). These stabilizers would also be used in the same manner as those of formulae (A), (B), (C) or (D). Again, however, stabilizers of formulae (A′), (B′), (C′) and (D′) are not within the presently claimed invention.

In any of the above structures, substituents for R and $R^1$ through $R^8$ can include halogen (such as chlorine, bromine, or fluorine), alkyl, alkenyl or aryl (except when specified to the contrary), a heterocyclic group, an aliphatic oxy group, an aromatic oxy group, an acyl group, an ester group, an amido group, an imido group, an imido group, a hydroxyl group, a cyano group, or a nitro group, any of the foregoing particularly having from 1 to 30 C atoms, more particularly 1 to 20 (and further particularly 1 to 10 or 1 to 5 C atoms).

Specific examples of stabilizers suitable for use in the present invention as well as some ether type stabilizers (within formula (A′), (B′), (C′) and/or (D′)) include, but are not limited to, the following:

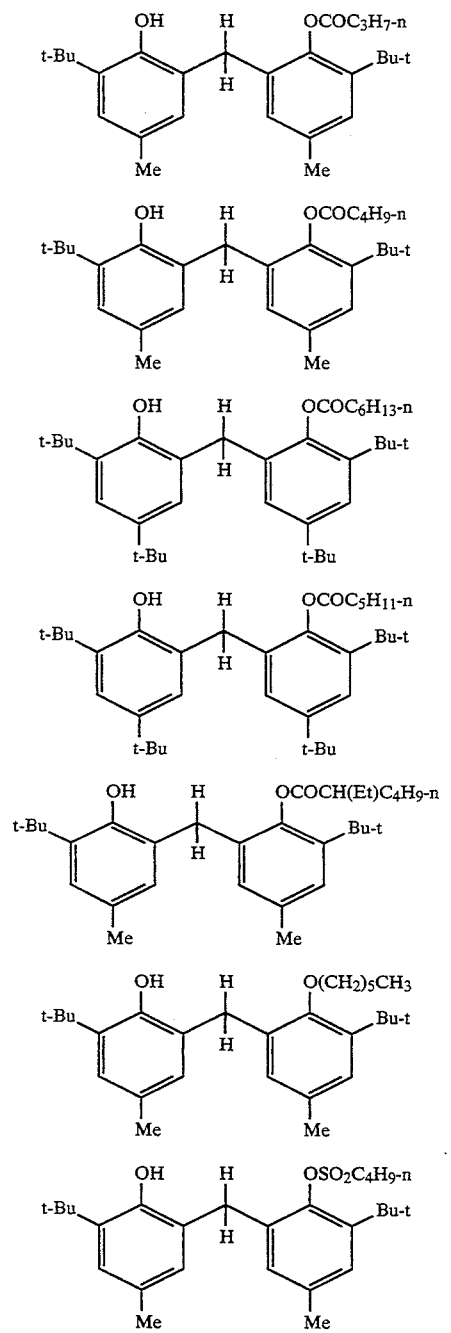

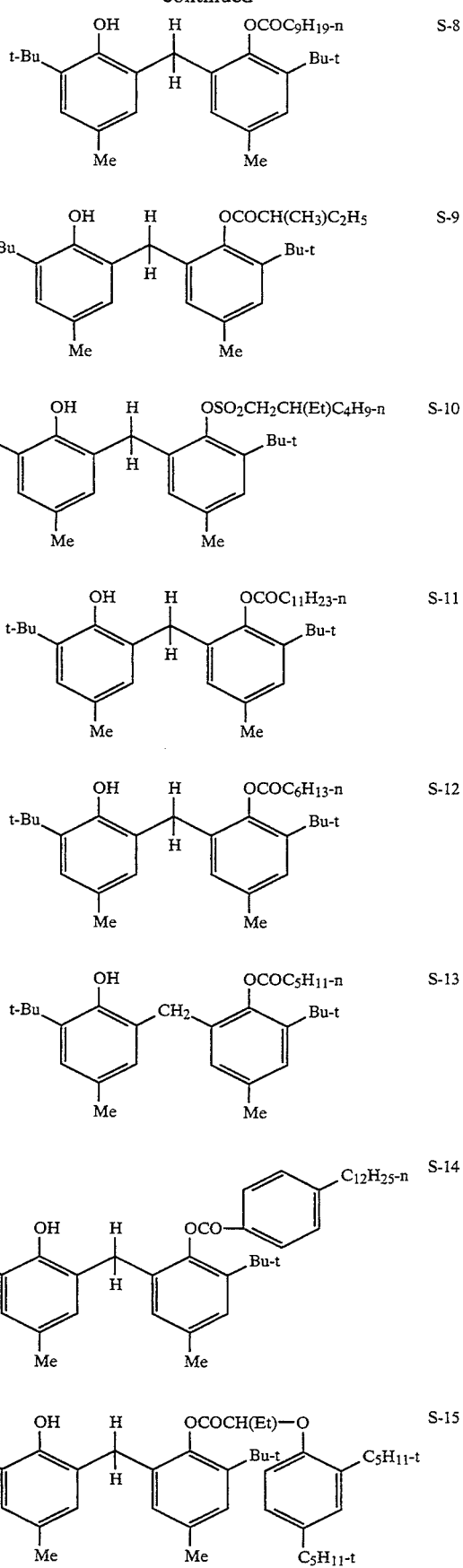

-continued

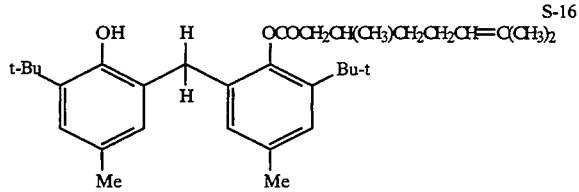
S-16

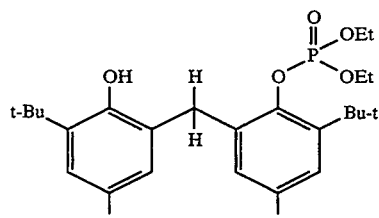
S-17

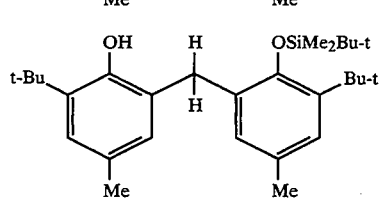
S-18

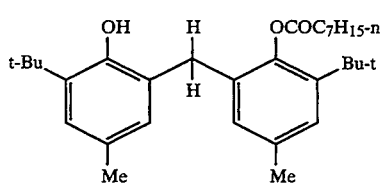
S-19

Particularly preferred stabilizers are the compounds of the formulae:

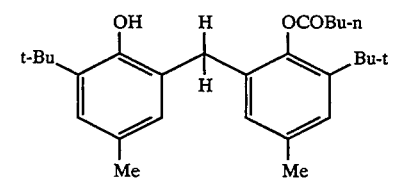
S-2

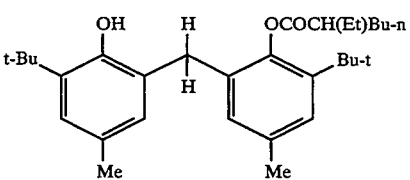
S-5

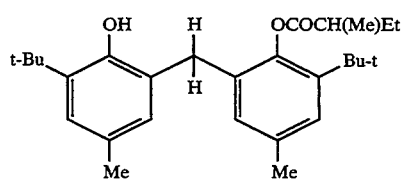
S-9

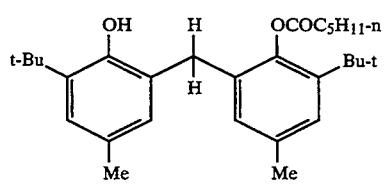
S-13

The dye-forming coupler is preferably a yellow dye-forming coupler of the following formula (E):

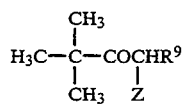
(E)

wherein:

R⁹ represents a substituted or unsubstituted N-phenylcarbamoyl group;

Z represents a hydrogen atom or a group releasable upon coupling with an oxidized product of a developing agent; and R⁹ and Z may form a dimer or a higher polymer.

Z can include a halogen atom, an aromatic azo group, and a group that connects a coupling active carbon and an aliphatic group, an aromatic group, a heterocyclic group, an aliphatic, aromatic, or heterocyclic sulfonyl group, or an aliphatic, aromatic, or heterocyclic carbonyl group via an oxygen, nitrogen, sulfur, or carbon atom. The aliphatic, aromatic, or heterocyclic group contained in these releasable groups may be substituted with various substituents. When they are substituted with two or more substituents, these substituents may be the same or different.

Specific examples of the coupling-releasable groups, Z, are a halogen atom (for example, a fluorine atom, a chlorine atom, a bromine atom, and the like), an alkoxy group (for example, an ethoxy group, a dodecyloxy group, a methoxyethylcarbamoylmethoxy group, a carboxypropyloxy group, a methylsulfonylethoxy group, and the like), an aryloxy group (for example, a 4-chlorophenoxy group, a 4-methoxyphenoxy group, a 4-carboxyphenoxy group, and the like), an acyloxy group (for example, an acetoxy group, a tetradecanoyloxy group, a benzoyloxy group, and the like), an aliphatic or aromatic sulfonyloxy group (for example, a methanesulfonyloxy group, a toluenesulfonyloxy group, and the like), an acylamino group (for example, a dichloroacetylamino group, a heptafluorobutyrylamino group, and the like), an aliphatic or aromatic sulfonamido group (for example, a methanesulfonamido group, a p-toluenesulfonylamino group, and the like), an alkoxycarbonyloxy group (for example, an ethoxycarbonyloxy group, a benzyloxycarbonyloxy group, and the like), an aryloxycarbonyloxy group (for example a phenoxycaronyloxy group, and the like), an aliphatic, aromatic or heterocyclic thio group (for example, an ethylthio group, a phenylthio group, a tetrazolylthio group, and the like), a carbamoylamino group (for example, and N-methylcarbamoylamino group, an N-phenylcarbamoylamino group, and the like), a 5- or 6-membered nitrogen-containing heterocyclic group (for example, an imidazolyl group, a pyrazolyl group, a triazolyl group, a tetrazolyl group, a 1,2-dihydo-2-oxo-1-pyridyl group, and the like), an imido group (for example, a succinimido group, a hydantoinyl group, and the like), an aromatic azo group (for example, a phenylazo group, and the like), and the like. These groups may be substituted with various substituents. The releasable group bonded to the coupling carbon via a carbon atom includes a bis-type coupler obtainable by a condensation reaction of an aldehyde or ketone with a four-equivalent coupler. The releasable group according to the present invention may contain other photographically useful groups, such as a group capable of forming a development restrainer, a development accelerator, and the like.

$R_9$ preferably includes a group represented by the formula (G):

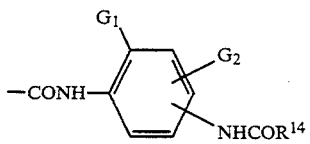

wherein $G_1$ represents a halogen atom or an alkoxy group or aryloxy group; $G_2$ represents a hydrogen atom, a halogen atom, or a substituted or unsubstituted alkoxy group; and $R^{14}$ represents a substituted or unsubstituted alkyl group. Typical examples of the substituent for $G_2$ or $R^{14}$ in the formula (G) includes an alkyl group, an alkoxy group, an aryl group, an aryloxy group, an amino group, a dialkylamino group, a heterocyclic group (for example, an N-morpholino group, an N-piperidino group, a 2-furyl group, and the like), a halogen atom, a nitro group, a hydroxyl group, a carboxyl group, a sulfo group, an alkoxycarbonyl group, and the like.

Yellow dye forming couplers of the type of formula (E) are well known in the art, and are described, for example in U.S. Pat. No. 4,748,100, U.S. Pat. No. 4,840,878, and EP 0 298 321. The method of preparation of such couplers and the method of use by dissolving them in solvents which are dispersed in photographic element emulsions, are also described in the foregoing references and the references cited in them. It will be noted that in preparation of elements of the present invention, the stabilizers are typically co-dispersed in the same solvent.

It is particularly preferred that the yellow dye-forming couplers be of the type of formula (F) below:

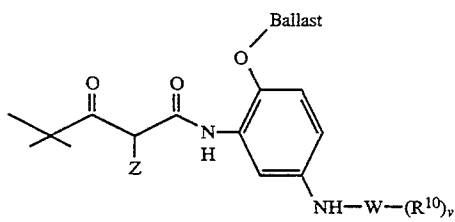

wherein:
$R^{10}$ is a substituted or unsubstituted alkyl group of 1 to 4 carbon atoms;
W is CO, $PO_3$ or $SO_2$;
Z is a substituted or unsubstituted aryloxy group releasable upon coupling with an oxidized product of a developing agent;
v is 1 or, when W is $PO_3$ v is 2;
Ballast is a ballast group which renders the coupler nondiffusible in the element.

The Ballast group preferably comprises substituted or unsubstituted alkyl and/or aryl moieties optionally linked by ether or ester groups. In a preferred group of couplers, the ballast group comprises an aryl moiety substituted with one or more alkyl groups, for example, alkyl groups containing 4–10 carbon atoms. Any of the foregoing groups may be substituted or unsubstituted. Examples of ballast groups that may be employed are:

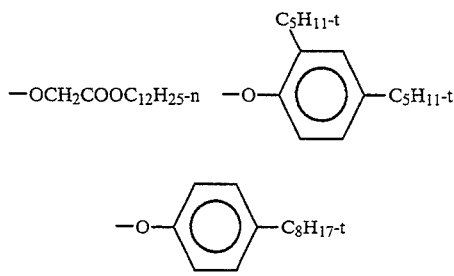

The coupling-off group Z may preferably be a phenoxy group optionally substituted with alkyl or arylsulfonyl, alkylsulfonamido, or alkoxycarbonyl groups which themselves are optionally substituted. Preferred coupling-off groups are phenoxy groups containing electron-withdrawing substituents at the ortho- and/or para-positions, especially at the para- and one ortho-position. In addition, ionizable substituents are also beneficial. Such preferred yellow couplers and their preparation and use are described in U.S. Pat. No. 5,021,333. A particularly preferred yellow dye-forming coupler has the following structure:

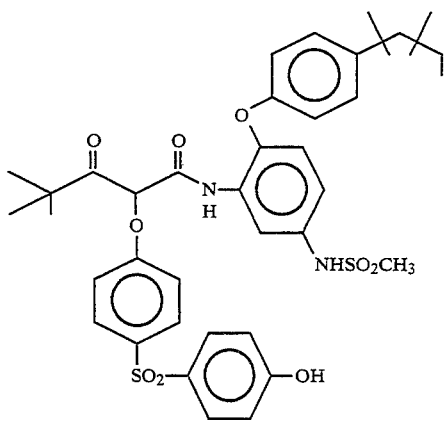

The photographic elements of the present invention can be single color elements or multicolor elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In a alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler, at least one of the couplers in the element being a coupler. The element can contain additional layers, such as filter layers, interlayers, overcoat layers, subbing layers, and the like.

In the following discussion of suitable materials for use in elements of this invention, reference will be made to *Research Disclosure*, December 1989, Item 308119, published by Kenneth Mason Publications, Ltd., Dudley Annex, 12a North Street, Emsworth, Hampshire P010 7DQ, ENGLAND, which will be identified hereafter by the term "Research Disclosure I." The Sections hereafter referred to are Sections of the Research Disclosure I.

The silver halide emulsions employed in the elements of this invention can be either negative-working or positive-working. Suitable emulsions and their preparation as well as methods of chemical and spectral sensitization are described in Sections I through IV. Color materials and development modifiers are described in Sections V and XXI. Vehicles which can be used in the elements of the present invention are described in Section IX, and various additives such as brighteners, antifoggants, stabilizers, light absorbing and scattering materials, hardeners, coating aids, plasticizers, lubricants and matting agents are described, for example, in Sections V, VI, VIII, X, XI, XII, and XVI. Manufacturing methods are described in Sections XIV and XV, other layers and supports in Sections XIII and XVII, processing methods and agents in Sections XIX and XX, and exposure alternatives in Section XVIII.

Preferred color developing agents are p-phenylenediamines. Especially preferred are:
-amino N,N-diethylaniline hydrochloride,
-amino-3-methyl-N,N-diethylaniline hydrochloride,
-amino-3-methyl-N-ethyl-N-(b-(methanesulfonamido)ethyl)aniline sesquisulfate hydrate,
4-amino-3-methyl-N-ethyl-N-(b-hydroxyethyl)aniline sulfate,
4-amino-3-b-(methanesulfonamido)ethyl-N,N-diethylaniline hydrochloride and
4-amino-N-ethyl-N-(2-methoxyethyl)-m-toluidine di-p-toluene sulfonic acid.

With negative working silver halide a negative image can be formed. Optionally a positive (or reversal) image can be formed.

The photographic elements of the present may also use colored couplers (e.g. to adjust levels of interlayer correction) and masking couplers such as those described in EP 213.490; Japanese Published Application 58-172,647; U.S. Pat. No. 2,983,608; German Application DE 2,706,117C; U.K. Patent 1,530,272; Japanese Application A-113935; U.S. Pat. No. 4,070,191 and German Application DE 2,643,965. The masking couplers may be shifted or blocked.

The photographic elements may also contain materials that accelerate or otherwise modify the processing steps e.g. of bleaching or fixing to improve the quality of the image. Bleach accelerators described in EP 193,389; EP 301,477; U.S. Pat. No. 4,163,669; U.S. 4,865,956; and U.S. Pat. No. 4,923,784 are particularly useful. Also contemplated is the use of nucleating agents, development accelerators or their precursors (UK Patent 2,097,140; U.K. Patent 2,131,188); electron transfer agents (U.S. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The elements may also contain filter dye layers comprising colloidal silver sol or yellow and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543,323.) Also, the couplers may be blocked or coated in protected form as described, for example, in Japanese Application 61/258,249 or U.S. Pat. No. 5,019,492.

The photographic elements may further contain image-modifying compounds such as "Developer Inhibitor Releasing" compounds (DIR's). Useful DIR's for elements of the present invention, are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612; 401,613.

DIR compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference.

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. The emulsions and materials to form elements of the present invention, may be coated on pH adjusted support as described in U.S. Pat. No. 4,917,994; with epoxy solvents (EP 0 164 961); with additional stabilizers (as described, for example, in U.S. Pat. No. 4,346,165; U.S. Pat. No. 4,540,653 and U.S. Pat. No. 4,906,559); with ballasted chelating agents such as those in U.S. Pat. No. 4,994,359 to reduce sensitivity to polyvalent cations such as calcium; and with stain reducing compounds such as described in U.S. Pat. No. 5,068,171 and U.S. Pat. No. 5,096,805. Other compounds useful in the elements of the invention are disclosed in Japanese Published Applications 83-09,959; 83-62,586; 90-072,629, 90-072,630; 90-072,632; 90-072,633; 90-072,634; 90-077,822; 90-078,229; 90-078,230; 90-079,336; 90-079,338; 90-079,690; 90-079,691; 90-080,487; 90-080,489; 90-080,490; 90-080,491; 90-080,492; 90-080,494; 90-085,928; 90-086,669; 90-086,670; 90-087,361; 90-087,362; 90-087,363; 90-087,364; 90-088,096; 90-088,097; 90-093,662; 90-093,663; 90-093,664; 90-093,665; 90-093,666; 90-093,668; 90-094,055; 90-094,056; 90-101,937; 90-103,409; 90-151,577.

The silver halide used in the photographic elements of the present invention may be silver bromoiodide, silver bromide, silver chloride, silver chlorobromide, silver chlorobromo-iodide, and the like. The type of silver halide grains preferably include polymorphic, cubic, and octahedral. The grain size of the silver halide may have any distribution known to be useful in photographic compositions, and may be ether polydipersed or monodispersed. Particularly useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T = ECD/t^2$$

where
ECD is the average equivalent circular diameter of the tabular grains in microns and
t is the average thickness in microns of the tabular grains.

The average useful ECD of photographic emulsions can range up to about 10 microns, although in practice emulsion ECD's seldom exceed about 4 microns. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micron) tabular grains. To achieve the lowest levels of granularity it is preferred to that aim tabular grain projected areas be satisfied with ultrathin (t<0.06 micron) tabular grains. Tabular grain thicknesses typically range down to about 0.02 micron. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micron.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions tabular grains satisfying the stated thickness criteria above account for at least 70 percent of the total grain projected area. In the highest performance tabular grain emulsions tabular grains satisfying the thickness criteria above account for at least 90 percent of total grain projected area.

Suitable tabular grain emulsions can be selected from among a variety of conventional teachings, such as those of the following: *Research Disclosure*, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The silver halide grains to be used in the invention may be prepared according to methods known in the art, such as those described in *Research Disclosure I* and James, *The Theory of the Photographic Process*. These include methods such as ammoniacal emulsion making, neutral or acid emulsion making, and others known in the art. These methods generally involve mixing a water soluble silver salt with a water soluble halide salt in the presence of a protective colloid, and controlling the temperature, pAg, pH values, etc, at suitable values during formation of the silver halide by precipitation.

The silver halide to be used in the invention may be advantageously subjected to chemical sensitization with compounds such as gold sensitizers (e.g., aurous sulfide) and others known in the art. Compounds and techniques useful for chemical sensitization of silver halide are known in the art and described in *Research Disclosure I* and the references cited therein.

The photographic elements of the present invention, as is typical, provide the silver halide in the form of an emulsion. Photographic emulsions generally include a vehicle for coating the emulsion as a layer of a photographic element. Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), gelatin derivatives (e.g., acetylated gelatin, phthalated gelatin, and the like), and others as described in *Research Disclosure I*. Also useful as vehicles or vehicle extenders are hydrophilic water-permeable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers, and the like, as described in *Research Disclosure I*. The vehicle can be present in the emulsion in any amount useful in photographic emulsions. The emulsion can also include any of the addenda known to be useful in photographic emulsions. These include chemical sensitizers, such as active gelatin, sulfur, selenium, tellurium, gold, platinum, palladium, iridium, osmium, rhenium, phosphorous, or combinations thereof. Chemical sensitization is generally carried out at pAg levels of from 5 to 10, pH levels of from 5 to 8, and temperatures of from 30° to 80° C., as illustrated in *Research Disclosure*, June 1975, item 13452 and U.S. Pat. No. 3,772,031.

The silver halide may be sensitized by sensitizing dyes by any method known in the art, such as described in *Research Disclosure I*. The dye may be added to an emulsion of the silver halide grains and a hydrophilic colloid at any time prior to (e.g., during or after chemical sensitization) or simultaneous with the coating of the emulsion on a photographic element. The dye/silver halide emulsion may be mixed with a dispersion of color image-forming coupler immediately before coating or in advance of coating (for example, 2 hours).

Photographic elements of the present invention may also usefully include a magnetic recording material as described in *Research Disclosure*, Item 34390, November 1992.

The following examples illustrate preparation of stabilizers used in elements of the present invention, and their beneficial characterisitics.

Stabilizer Preparation

The general process of synthesizing stabilizers of the type of formula (III) below, comprises reacting a bisphenol of the formula (I) with an electrophilic reagent of the formula (II) in the presence of a suitable base in the absence or presence of a suitable solvent to obtain the mono-blocked stabilizer of the formula (III).

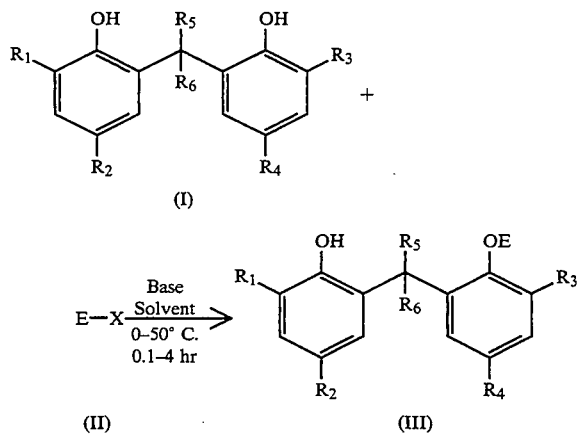

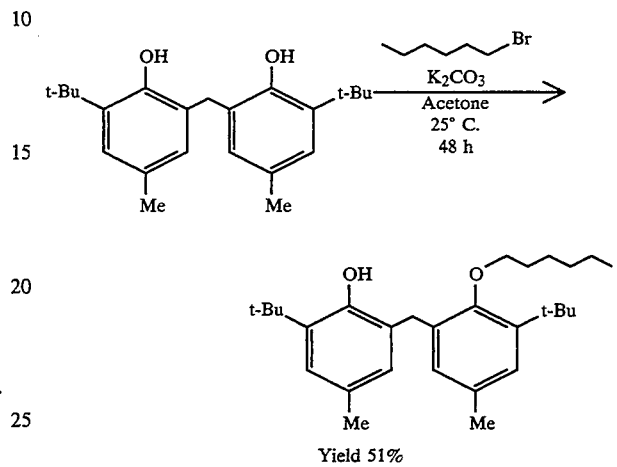

Yield 51%

A variety of electrophiles, E–X, may be employed to generate stabilizers of formula (III) type above, with diverse structural features. Formula (III) stabilizers include stabilizers of the type of the present invention, namely formula (A) stabilizers, although the same general reaction may be used to produce other stabilizers of formula (III). The electrophiles, E–X, may braodly include: alkylating agents, silylating agents, acylating agents, aroylating agents, sulfonylating agents, as well as phosphorylating agents. Of these, acylating agents, aroylating agents, sulfonylating agents, and phosphorylating agents are used in order to produce stabilizers of formula (A). These latter reagents are "reactive" elecrophiles and afford the corresponding stabilizers in higher yields and in shorter reaction times than alkylating agents.

A majority of the electrophiles will require a base for the formation of mono-blocked bis-phenol derivatives. Preferred bases are inorganic reagents such as potassium carbonate, strontium carbonate; organic bases like triethylamine, pyridine, N,N-dialkylanilines, etc.

Preparation of a stabilizer of formula (III) is preferably conducted in the presence of a wide range of solvents that are inert with respect to the reactants and products and satisfactorily dissolve the reactants: hydrocarbons, ethers, esters, amides, sulfoxides, etc. Preferred reaction temperatures are in the range of 0° to 50° C. and the reaction times are in the range of 0.1 to 4 h.

Of the "reactive" electrophiles described above to produce stabilizers of formula (A), preferred reagents are the highly reactive acylating agents such as acyl halides, acyl anhydrides, and acylheterocycles (acylimidazoles). More preferable reagents are acyl chlorides having a chain length $C_4$–$C_{30}$.

Among the variety of suitable solvents, preferred solvents are carboxylic acid esters, the most preferred being ethyl acetate. Use of ethyl acetate as the solvent affords improved selectivity of monoacylation over diacylation thereby leading to purer and more readily isolable desired product.

The preferred reaction conditions involve the concentration of reactants in the range of 0.6 to 2.0M, ratio of bis-phenol to acyl halide to be in the range of 1.0 to 1.1, ratio of bis-phenol to base in the range of 0.5 to 0.7 and the reaction temperature to be in the range of 0° to 25° C.

The desired stabilizer product can be isolated via both aqueous as well as non-aqueous work-up procedures. In cases where the stabilizer is highly soluble in ethyl acetate, non-aqueous procedure is the most preferred methodology; filtration of triethylamine hydrochloride and removal of ethyl acetate solvents routinely afforded the stabilizer in high purity and yield, to be directly utilized for photographic dispersion making.

Details of synthesis of particular stabilizers of the type of formula (III) are given below:
Reaction of Bisphenol with n-Hexyl Bromide. Synthesis of S-6.

A 100-mL 1-neck flask equipped with a magnetic stirring bar and a pressure equalized addition funnel was charged with 2,2'-methylenebis[4-methyl-6-(tert-butyl)-phenol] shown above (15.09 g, 44.3 mmol), acetone (75 mL), and milled $K_2CO_3$ (9.19 g, 66.5 mmol). The addition funnel was charged with n-hexyl bromide (6.85 mL, 48.7 mmol). The alkyl bromide was then added dropwise over 5 min to the acetone solution and the resulting mixture vigorously stirred at room temperature. After 1 h, a tlc analysis (20:1 ligroin 950/EtOAc) showed only the presence of starting material. After 2 h, an aliquot was removed and following an aqueous workup the $^1$H NMR shows only the presence of starting materials in a 1:1 ratio. After 3 h, the reaction mixture became purple in color. The intensity of the purple color increased over the course of the reaction. Tlc analysis showed a trace amount of a new less polar spot and a major spot for the bisphenol starting material. After a 16 h period, an aliquot was removed and after an aqueous workup the $^1$H NMR showed 50% conversion of bisphenol to mono-alkylated product. A catalytic amount (1%) of anhydrous KI was added and the reaction was stirred over night. After 48 hrs, tlc analysis revealed the reaction to be still incomplete. The insoluble salts were collected by suction filtration and the filtrate was stripped to give a purple oil, dissolved in diethyl ether and partitioned with acidic water (1% HCl) which gave a yellow bilayer. The ethereal layer was separated and the aqueous layer was extracted with $ET_2O$ (2×100 mL). Organic layers were washed with brine (1×100 mL), dried over anhydrous $MgSO_4$, treated with Darco®, and filtered. Removal of solvents on rotatory evaporator followed by evacuation under high vacuum (0.2–0.4 mm Hg) gave a yellow oil (18.01 g) which was purified by flash chromatography over silica gel (24×13 cm) with 10% EtOAc in Ligroin 950 as eluent to give a yellow oil (9.62 g, 51%). $^1$H NMR (300 MHz) CDCl$_3$: δ0.94 (m, 3H), 1.35 (s, 8H), 1.40 (br. s, 14 H), 1.57 (m, 2H), 2.01 (m, 2H), 2.25 (s, 3H), 2.29 (s, 3H), 3.82 (s, 2H), 3.99 (t, J=7.0 Hz, 2 H), 5.29 (s, 1H, —OH), 6.97 (m, 3H), 7.49 (s, 1H).

Reaction of Bisphenol with n-Hexanoyl Chloride in Di-ethyl Ether using an Aqueous Workup. Synthesis of S-13.

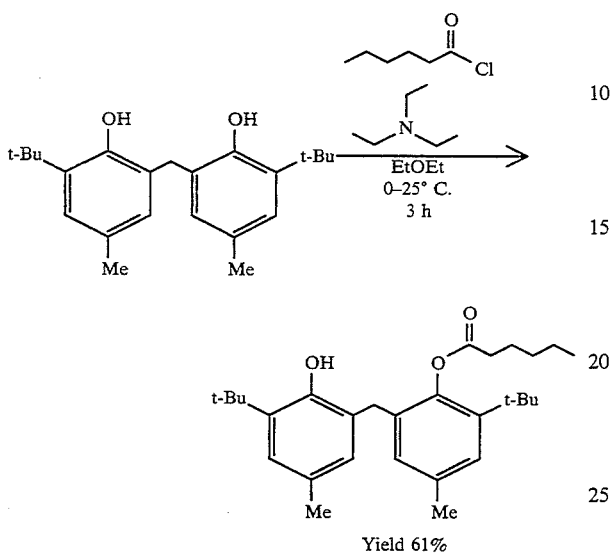

Yield 61%

A 250-mL 1-neck flask equipped with a magnetic stirring bar, and a pressure equalized addition funnel was charged with 2,2'-methylenebis[4-methyl-6-(tert-butyl)-phenol] (5.04 g, 14.8 mmol), ET$_2$O (25 mL), and Et$_3$N (3.1 mL, 22.2 mmol). This solution was chilled in an ice/MeOH bath for 10 min while stirring under an Argon atmosphere. The addition funnel was charged with hexanoyl chloride (2.17 mL, 15.5 mmol) and the acid chloride was added dropwise over 5 min to the ET$_2$O solution. A white precipitate formed on addition (Et$_3$N:HCl). The reaction was stirred in an ice-bath for 1 h warming slowly to room temperature, and stirred at room temperature for 1 h when tlc analysis (10:1 ligroin 950/EtOAc) showed a trace of starting material and a major spot for desired product. After stirring for another 2 h at room temperature, tlc analysis showed complete conversion of starting material. The reaction mixture was poured into 350 mL of acidic (1% HCl) ice-water with an additional 100 mL of Et$_2$O, and transferred to a separatory funnel. Layers were separated and the aqueous layer was extracted with ET$_2$O (2×100 mL). The organic layers were combined, washed with brine (1×200 mL), dried over anhydrous MgSO$_4$, filtered and stripped to give an amber oily residue. $^1$H NMR analysis of the crude product mixture revealed the ratio of mono- to di-acylated products to be 93:7. Upon standing a white crystalline solid formed which was recrystallized from anhydrous ethanol. Two crops were collected on a glass frit and washed with cold (0° C.) anhydrous ethanol, and dried at 60° C. overnight in a vacuum oven, to give 3.98 g (61%) of the desired pure mono-acylated product as a white crystalline powder, mp. 85°-87° C.; $^1$H NMR (300 MHz) CDCl$_3$: δ0.94 (t, J=6.9 Hz, 3H), 1.37 (s, 9H), 1.40 (br. s, 13H), 1.83 (m, 2H), 2.22 (s, 3H), 2.31 (s, 3H), 2.68 (m, 2H), 3.64 (s, 2H), 5.28 (s, 1H, —OH), 6.66 (s, 1H), 6.85 (s, 1H), 7.06 (s, 1H), 7.10 (s, 1H).

Reaction of Bisphenol with n-Hexanoyl Chloride in Ethyl Acetate using an Aqueous Workup. Synthesis of S-13.

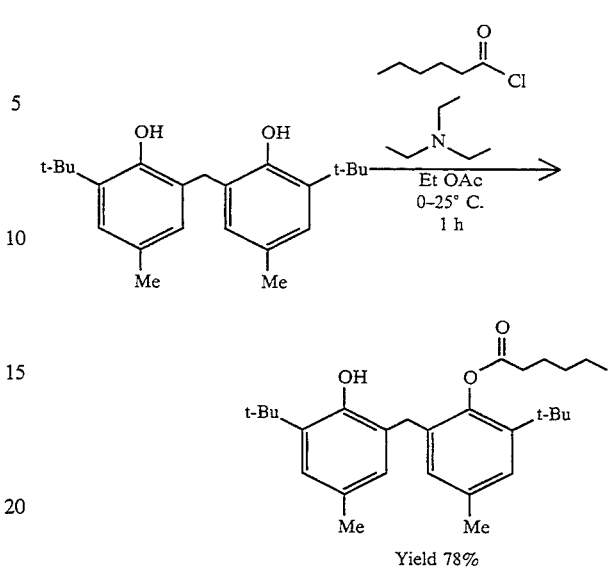

Yield 78%

A 1 L 1-neck flask equipped with a magnetic stirring bar and a pressure equalized addition funnel was charged with 2,2'-methylenebis[4-methyl-6-(tert-butyl)-phenol] (70.92 g, 208.28 mmol), EtOAc (350 mL), and Et$_3$N (43.5 mL, 312.42 mmol). This solution was chilled in a ice/water bath for 10 min while stirring under an Argon atmosphere. The addition funnel was charged with hexanoyl chloride (29.1 mL, 208.28 mmol). The acid chloride was then added dropwise over 10 min to the EtOAc solution. A white precipitate formed on addition (Et$_3$N:HCl). Upon completion of addition the ice bath was removed and the reaction mixture was allowed to warm to room temperature while stirring. After 1 h an aliquot was removed and quenched into water and extracted with Et$_2$O. A tlc (20:1 ligroin 950/EtOAc) of the ethereal layer showed complete conversion of starting material to a new spot. The reaction mixture was poured into 800 mL of ice water, and was transferred to a seperatory funnel with 250 mL of Et$_2$O. This gave an inseparable emulsion. However, addition of a small amount of dilute HCl (1%) gave an easily separable bilayer. The organic layer was set aside and the aqueous layer was extracted with diethyl ether(2×250 mL). Combined organic layers were washed with brine (1×300 mL), dried over anhydrous MgSO$_4$, treated with Darco ®, and filtered. Removal of solvents on rotatory evaporator followed by evacuation under high vac (0.2-0.4 mm Hg) gave a thick viscous mass (93.4 g, quantitative yield). After standing over night at room temperature a white crystalline material began to form, which upon trituration completely crystallized to give a white flakey solid. $^1$H NMR analysis of crude product mixture revealed the ratio of mono- to di-acylated products to be 97:3, respectively. Recrystallization from anhydrous ethanol with cooling in a −10° C. ice/MeOH bath gave a white crystalline solid. Two crops were collected on a glass frit and washed with cold (0° C.) anhydrous ethanol, and dried at 40° C. for 72 h in vacuum oven, afforded 71.25 g (78%) of a white crystalline powder; mp. 84°-85° C. FDMS m/e=438. 1H NMR (300 MHz) CDCl$_3$: δ0.94 (t, J=6.9 Hz, 3H), 1.37 (s, 9H), 1.40 (br. s, 13H), 1.83 (m, 2H), 2.22 (s, 3H), 2.31 (s, 3H), 2.68 (m, 2H), 3.64 (s, 2H), 5.28 (s, 1H, OH), 6.66 (s, 1H), 6.85 (s, 1H), 7.06 (s, 1H), 7.10 (s, 1H). Anal. Calcd for $C_{29}H_{42}O_3$: C, 79.41; H, 9.65. Found: C, 79.48; H, 9.93.

Similarly, the effect of reaction solvent on the ratio of mono- to diacylated products was determined by $^1$H NMR spectroscopy and the results are summarized in Table 1. In each case the reaction was taken to completion. All reactions for Table 1 were aqueous workup with the exception of SC-3 in EtOAc which was non-aqueous workup. By aqueous workup is meant that the reaction mixture, following reaction, is contacted with water or an aqueous solution in order to separate the organic products. By non-aqueous workup is meant that the reaction mixture is filtered and the product recovered therefrom by solvent removal followed by crystallization.

TABLE 1

[Structure: 2,2'-methylenebis[4-methyl-6-(tert-butyl)-phenol] with one OH and one OE group, t-Bu and Me substituents]

| (Number) | E | Ratio: mono-acylated/di-acylated product* | |
|---|---|---|---|
| | | $Et_2O$ | EtOAc |
| (SC-3) | n-propionyl | 33/66 | 93/7 |
| (S-1) | n-butyryl | — | 90/10 |
| (S-2) | n-valeryl | 80/20 | — |
| (S-13) | n-hexanoyl | 93/7 | 97/3 |
| (S-19) | n-octanoyl | 83/17 | 95/5 |
| (S-8) | n-decanoyl | 85/15 | 95/5 |

*Ratios determined from relative integration of crude product mixtures observed in $^1$H NMR.

It is clearly evident from the results summarized in Table 1 that a better selectivity of mono-acylation is achieved with ester solvents, such as ethyl acetate, than ethereal solvents, such as diethyl ether.

Reaction of Bisphenol with 2-Ethylhexanoyl Chloride in Ethyl Acetate using an Aqueous Workup. Synthesis of S-5.

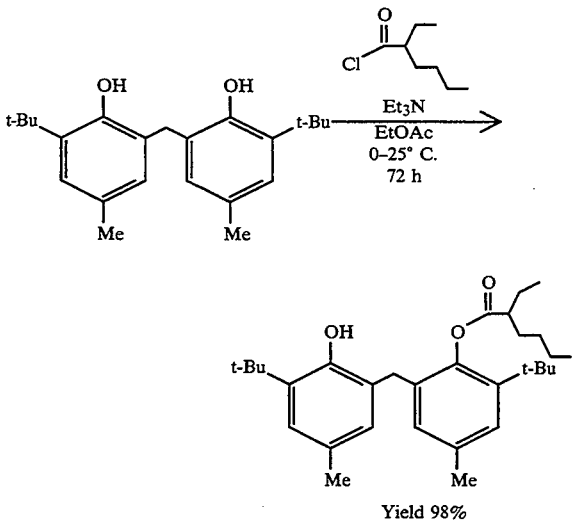

Yield 98%

A 250 mL 1-neck flask equipped with a magnetic stirring bar and a nitrogen bubbler, was charged with 2-ethylhexanoic acid (36.52 mL, 220 mmol), oxalyl cholride (93.5 mL, 242 mmol), and several drops of anhydrous DMF. This solution was solution was stirred for 1.5 hrs. at 25° C., then solvent was stripped on rotatory evaporator, and the resulting yellow oil was washed with ligrion 950 and then stripped afforded the 2-ethylhexanoyl chloride as a yellow oil in quantitative yield.

A 500 mL 3-neck flask equipped with magnetic stirring bar and a pressure equalized addition funnel, was charged with 2,2'-methylenebis[4-methyl-6-(tert-butyl)-phenol] (68.0 g, 200 mmol), EtOAc (100 mL), and $Et_3N$ (33 g, 300 mmol). This solution was cooled to 20° C. while stirring under a Nitrogen atmosphere. The addition funnel was charged with 2-ethylhexanoyl chloride (35.8 g, 220 mmol). The acid chloride was then slowly added dropwise to the EtOAc solution, and the resulting mixture was allowed to stir for 72 hrs, warming to 25° C. Tlc analysis (100% $CH_2Cl_2$) showed essentially complete conversion of starting material to a new spot. The reaction mixture was added to a mixture of conc. HCl (62.5 mL) and crushed ice (200 g), and the resulting mixture was transferred to a separatory funnel. The organic layer was separated and the aqueous layer was extracted with EtOAc (2×100 mL). The combined organic layers were washed with brine (1×150 mL), and dried (anhydrous $Na_2SO_4$). Removal of solvent yielded the desired stabilizer as a yellow viscous oil (95.75 g, quantitative yield). Column chromatography of crude product gave a colorless oil (92.14 g, 98%). $^1$H NMR ($CDCl_3$): δ1.07 (m, 3H), 1.11 (m, 3H), 1.43 (s, 9H), 1.45 (s, 9H), 1.54 (m, 2H), 1.73 (m, 3H), 1.94 (m, 3H), 2.25 (s, 3H), 2.36 (s, 3H), 2.72 (m, 1H), 3.68 (d, J=9.0 Hz, 2H), 5.43 (d, J=9.0 Hz, 1H, —OH), 6.67 (s, 1H), 6.89 (s, 1H), 7.12 (s, 1H), 7.15 (s, 1H).

Reaction of Bisphenol with Benzoyl Chloride in Ethyl Acetate using a Non-Aqueous Workup. Synthesis of SC-4.

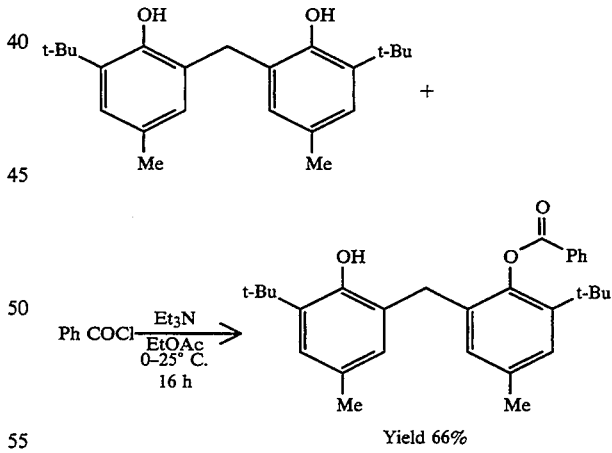

Yield 66%

A 100 mL 1-neck flask equipped with a magnetic stirring bar, and a pressure equalized addition funnel was charged with 2,2'-methylenebis[4-methyl-6-(tert-butyl)-phenol] (10.34 g, 30.4 mmol), EtOAc (50 mL), and $Et_3N$ (6.35 mL, 45.6 mmol). This solution was chilled in an ice/MeOH bath for 10 min while stirring under an Argon atmosphere. The addition funnel was charged with benzoyl chloride (3.56 mL, 30.7 mmol). The acid chloride was then added dropwise over 5 min to the EtOAc solution. A white precipitate formed on addition ($Et_3N$:HCl). The reaction was stirred in ice bath for 30 min., ice bath was removed and reaction was stirred at room temperature for 1.5 h. Tlc analysis (20:1 ligroin 950/EtOAc) showed partial conversion of starting material. An aliquot was removed and quenched into water, extracted with EtOAc, dried (MgSO4), and stripped to give a yellow residue. $^1$H NMR analysis shows 67% conversion of starting material to mono-aroylated product. There was no observed formation of di-aroylated product. Reaction was allowed to stir for 16 h at room temperature. Tlc analysis shows essentially complete conversion of starting material to new product. Reaction mixture was filtered, solids were washed with EtOAc and discarded, filtrate was stripped to give a pale yellow foam (11.74 g, 89%). Recrystallization from n-hexanes afforded a solid which was collected on frit, washed with cold n-hexanes, and dried at 90° C. in vacuo, to give 8.74 g (66%) of the desired pure monoacylated product as a off-white crystalline powder, mp 148°–150° C.; $^1$H NMR (300 MHz) CDCl3: δ1.39 (s, 9H), 1.40 (s, 9H), 2.25 (s, 3H), 2.26 (s, 3H), 3.72 (m, 2H), 5.37 (s, 1H, —OH), 6.74 (s, 1H), 6.80 (s, 1H), 7.03 (s, 1H), 7.17 (s, 1H), 7.55 (t, J=7.5 Hz, 2H), 7.68 (t, J=7.5 Hz, 1H), 8.27 (d, J=7.5 Hz, 2H).

It is clearly evident that the synthesis of aroyl derivatives require longer reaction times than acyl derivatives. Further, aroyl derivatives exhibit considerablely higher melting points.

Reaction of Bisphenol with n-Hexanoyl Chloride in Ethyl Acetate using a Non-Aqueous Workup Synthesis of S-13.

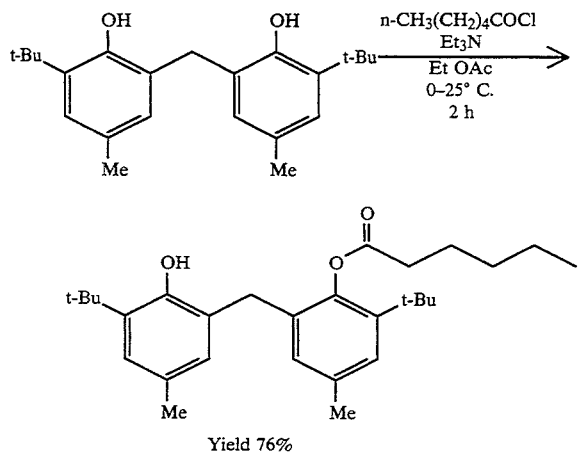

Yield 76%

A 500 mL 3-neck flask equipped with a magnetic stirring bar, digital thermometer probe and a pressure equalized addition funnel was charged with 2,2'-methylenebis[4-methyl-6-(tert-butyl)-phenol] (75.28 g, 221.1 mmol), EtOAc (110 mL), and Et3N (37 mL, 265.3 mmol). This solution was chilled in a ice/MeOH bath for 10 min while stirring under an Argon atmosphere (T=−1.1° C.). A pressure equalized addition funnel was charged with n-hexanoyl chloride (31.25 g, 232.1 mmol). The acid chloride was then added dropwise over 27 min to the EtOAc solution, at a controlled rate of 1.2 mL/min. The internal reaction temperature was observed to rise quickly if rate was not controlled. A white precipitate was formed on addition (Et3N:HCl). The temperature was recorded approximately once every minute over the course of the acid chloride addtion. Internal temperature during addtion ranged from −1.1° to 5.0° C. However, soon after the rate of addition was established the reaction temperature was mantained at 1° C.±1. The reaction was stirred for another 30 min at 0° C., and then the cold bath was removed and the reaction was allowed to warm to room temperature. After stirring at room temperature for 2 h tlc analysis (10:1 ligroin 950/EtOAc) showed essentially complete conversion of starting material to a new spot. Reaction mixture was filtered and white Et3N:HCl salts were washed with cold (15° C.) EtOAc, white solid was dried at 60° C. overnight in vacuum oven. Solid (31.79 g, 99.4 %) was confirmed as Et3N:HCl by $^1$H NMR and was free of any reaction products Filtrate and washings were combined and stripped to give an amber oily residue (98.5 g, essentially quantitative yield). $^1$H NMR of crude product shows ratio of mono- to di-acylated products to be 97:3, respectively, and was free of any trace of Et3N:HCl This amber viscous oil was dissolved in 110 mL of anhydrous ethanol and warmed to 70° C., filtered and chilled to 15° C., to give a white crystalline solid, which was collected by filtration, wahed with cold anhydrous ethanol and dried at 50° C. in a vacuum oven overnight, to give a white crystalline solid (68.21 g, 70%). Concentration of mother liquor and chilling gave an additional crop giving a total yield of 74.34 g (76%) of mono-acylated product, mp. 85°–87° C. FDMS m/e=438. $^1$H NMR (300 MHz) CDCl3: δ0.94 (t, J=6.9 Hz, 3H), 1.37 (s, 9H), 1.40 (br. s, 13H), 1.83 (m, 2H), 2.22 (s, 3H), 2.31 (s, 3H), 2.68 (m, 2H), 3.64 (s, 2H), 5.28 (s, 1H, —OH), 6.66 (s, 1H), 6.85 (s, 1H), 7.06 (s, 1H), 7.10 (s, 1H). Anal. Calcd for C29H42O3: C, 79.41; H, 9.65. Found: C, 79.30; H, 9.58.

Several other compounds were prepared in a similar fashion with varying alkyl chain length and substitution pattern. The method of workup and physical data for these compounds are given below in Table 2. All ractions were continued to completion.

TABLE 2

| Compound (Number) | Method of Work up Aqueous/Non-Aqueous | Yield (%) | Method of Purification | mp. °C. |
|---|---|---|---|---|
| • n-propionyl (SC-3) | Non-Aqueous | 72 | Rxtal | 105–107 |
| • benzoyl (SC-4) | Non-Aqueous | 66 | Rxtal | 148–150 |
| • n-butyryl (S-1) | Aqueous | 70 | Chromat. | oil |
| • 2-methylbutryl (S-2) | Non-Aqueous | 95 | Rxtal | 84–88 |
| • n-valeryl (S-2) | Aqueous | 60 | Chromat. | oil |
| • n-hexanoyl (S-13) | Aqueous | 78 | Rxtal | 84–85 |
| • n-hexanoyl (S-13) | Non-Aqueous | 76 | Rxtal | 85–87 |
| • 2-ethylhexanoyl (S-5) | Aqueous | 98 | Chromat. | oil |

TABLE 2-continued

| Compound (Number) | Method of Work up Aqueous/Non-Aqueous | Yield (%) | Method of Purification | mp. °C. |
|---|---|---|---|---|
| • n-heptanoyl (S-12) | Non-Aqueous | 71 | Chromat. | oil |
| • n-octanoyl (S-19) | Aqueous | 70 | Chromat. | oil |
| • n-decanoyl (S-8) | Aqueous | 70 | Chromat. | oil |
| • citronelloyl (S-16) | Non-Aqueous | 80 | Chromat. | oil |
| • n-butane sulfonate (S-7) | Aqueous | 50 | Chromat. | glass 45–49 |

† Diethyl ether used as reaction solvent.
Note,
in Table 2 above, "Chromat." = chromatography; "Rxtal" = recrystallization.

EXAMPLE 1

Crystallization Tests

In order to evaluate the tendency of various of the stabilizers to result in crystallization, dispersions of coupler, stabilizer and solvent in gelatin, were prepared by either of the two methods described below. Three different formulations, A, B and C, were prepared by the two methods as indicated in Table 4 below.

Method I: The quantities of each component used are found in Table 3. The quantities listed are weight ratios based on coupler quantity as 1.00 in each Formulation. In one vessel, the coupler, coupler solvent (dibutyl phthalate), stabilizer, and ethyl acetate were combined and warmed to dissolve. To this solution was added gelatin, surfactant, and water. After manual mixing the mixture was passed three times through a Gaulin colloid mill.

Method II: The quantities of the organic components are as in Method I. The coupler, coupler solvent (dibutyl phthalate), and stabilizer were combined and heated with gelatin, surfactant, and water. This mixture was then passed through a microfluidizer in the conventional way.

TABLE 3

| Component | Formulation A | Formulation B | Formulation C |
|---|---|---|---|
| Yellow Coupler Y-1 | 1.00 | 1.00 | 1.00 |
| Stabilizer | 0.44 | 0.86 | 1.10 |
| Solv-1 | 0.56 | 0.23 | 0.30 |
| Solv-2 | 0.00 | 0.23 | 0.30 |

The structures of the above yellow coupler and solvents are below:

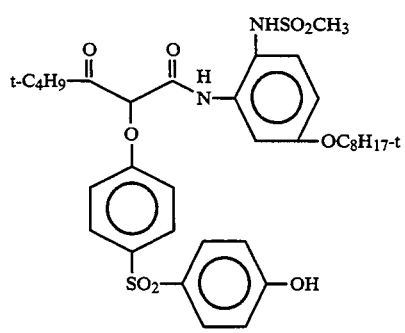

Y-1

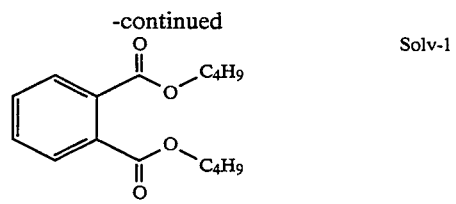

Solv-1

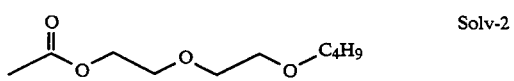

Solv-2

Comparative stabilizers which are used in this and other Examples below, have the following structures:

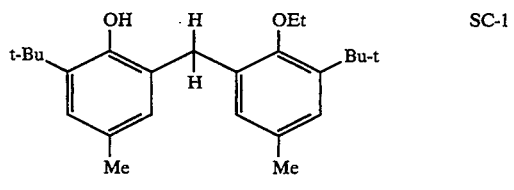

SC-1

Comparative Stabilizer

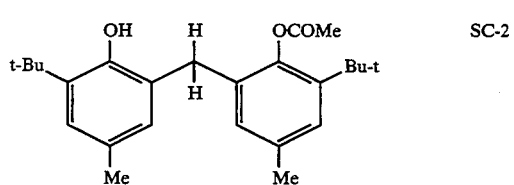

SC-2

Comparative Stabilizer

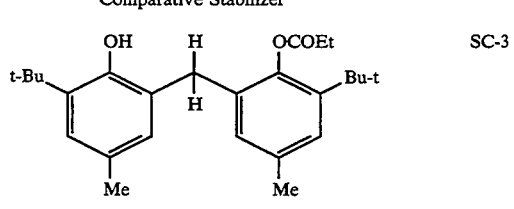

SC-3

Comparative Stabilizer

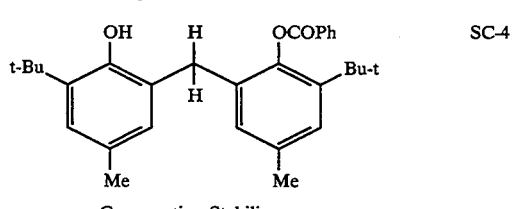

SC-4

Comparative Stabilizer

When the comparison stabilizer is used in formulation B and C with coupler Y-1 it precipitates. This undesirable precipitation is greatly enhanced when dispersions are incubated at warm temperatures for short time periods. The new stabilizers demonstrate a significant advantage for this parameter. Table 4 shows data for the dispersions along with stabilizer melting points and whether crystallization occurs or not ("Yes" under "Crystals" means crystallization occurred; "No" means no crystallization occurred).

TABLE 4

| Stabilizer | Dispersion Method | Formulation | Hold Time | Melting Point (°C.) | Crystals |
|---|---|---|---|---|---|
| SC-1 | Comp. | I | A | 24 h | 132–135 | Yes |
| " | | I | B | 24 h | 132–135 | Yes |
| " | | I | C | 24 h | 132–135 | Yes |
| SC-2 | Comp. | II | B | 24 h | 111–113 | Yes |
| " | | I | C | 96 h | 111–113 | Yes |
| SC-3 | Comp. | I | B | 24 h | 105–107 | Yes |
| S-5 | Invt. | I | B | 96 h | liquid | No |
| " | " | I | C | 96 h | liquid | No |
| " | " | II | B | 24 h | liquid | No |
| S-9 | Invt. | I | B | 96 h | 84–88 | No |
| " | " | II | B | 24 h | 84–88 | No |
| " | " | I | C | 96 h | 84–88 | No |
| S-13 | Invt. | I | B | 96 h | 84–85 | No |
| " | " | I | C | 96 h | 84–85 | No |
| " | " | II | B | 24 h | 84–85 | No |
| S-2 | Invt. | I | B | 96 h | liquid | No |
| " | " | I | C | 96 h | liquid | No |
| S-7 | Invt. | I | C | 24 h | 45–49 (glass) | No |

Stab. = Stabilizer; Comp. = Comparison; Invt. = Invention

EXAMPLE 2

Photographic Element Examples

Photographic elements were prepared using the Formulations of Table 3, by coating the following layers in the order listed on a resin-coated paper support:

| 1st layer | |
|---|---|
| Gelatin | 300 mg/ft$^2$ |
| 2nd layer | |
| Gelatin | 150 mg/ft$^2$ |
| A sufficient amount of a Formulation to provide Coupler level at (stabilizer and solvent levels - see Table 3) | 50 mg/ft$^2$ |
| Blue sensitized AgCl emulsion | 23 mg/ft$^2$ |
| 3rd layer | |
| Gelatin | 124 mg/ft$^2$ |
| 2-(2H-benzotriazol-2-yl)-4,6-bis-(1,1-dimethylpropyl)phenol | 68 mg/ft$^2$ |
| Tinuvin 326 ™ (Ciba-Geigy) | 12 mg/ft$^2$ |
| 4th layer | |
| Gelatin | 130 mg/ft$^2$ |
| Bis(vinylsulfonylmethyl) ether | 12.6 mg/ft$^2$ |

Exposing And Processing of the Photographic Elements

The photographic elements were given stepwise exposures to blue light and processed as follows at 35° C.

| Developer | 45 seconds |
|---|---|
| Bleach-Fix | 45 seconds |
| Wash (running water) | 1 minute, 30 seconds |

The developer and bleach-fix were of the following compositions:

| Developer | |
|---|---|
| Water | 700.00 mL |
| Triethanolamine | 12.41 g |
| Blankophor REU ™ (Mobay Corp.) | 2.30 g |
| Lithium polystyrene sulfonate (30%) | 0.30 g |
| N,N-Diethylhydroxylamine (85%) | 5.40 g |
| Lithium sulfate | 2.70 g |
| N-{2-[(4-amino-3-methylphenyl) ethylamino]ethyl}methanosulfonamide sesquisulfate | 5.00 g |
| 1-Hydroxyethyl-1,1-diphosphonic acid (60%) | 0.81 g |
| Potassium carbonate, anhydrous | 21.16 g |
| Potassium chloride | 1.60 g |
| Potassium bromide | 7.00 mg |
| Water to make | 1.00 L |
| pH @ 26.7° C. adjusted to 10.04 +/− 0.05 | |
| Bleach-Fix | |
| Water | 700.00 mL |
| Solution of ammonium thiosulfate (54.4%) + ammonium sulfite (4%) | 127.40 g |
| Sodium metabisulfite | 10.00 g |
| Acetic acid (glacial) | 10.20 g |
| Solution of ammonium ferric ethylenediaminetetraacetate (44%) + ethylenediaminetetraacetic acid (3.5%) | 110.40 g |
| Water to make | 1.00 L |
| pH @ 26.7 °C. adjusted to 5.5 +/− 0.1 | |

Yellow dyes were formed in the photographic elements upon processing. The following photographic characteristics were determined: Status A D$_{max}$ (the maximum density to blue light); Speed (the relative log exposure required to yield a density to blue light of 1.0); and Contrast (the ratio (S-T)/0.6, where S is the density at a log exposure 0.3 units greater than the Speed value and T is the density at a log exposure 0.3 units less than the Speed value). Status A D$_{max}$ values are provided for the elements containing the indicated stabilizers in Table 5 below. All elements for which data are provided in Table 5 contained coupler dispersion Formulation B from Table 3 above, which was prepared by method I (although no significant variation in results was noted when the dispersions were prepared by method II).

TABLE 5

| Stabilizer | $D_{max}$ |
| --- | --- |
| Comparison (SC-2) | 2.09 |
| Invention 1 (S-5) | 2.33 |
| Invention 2 (S-9) | 2.26 |

As can be seen from Table 5, stabilizers of the present invention provided higher $D_{max}$ after coating, exposure and development as described above.

EXAMPLE 3

Photographic Element Examples

The stabilizers of this invention also improve the light stability of the yellow dye that is formed in processing. To demonstrate this, photographic elements were prepared, exposed and processed as outlined in Example 2 above using Formulation B. The elements were were tested for fading. In each case the test was done by irradiating the sample with a light from a high intensity Xenon light source. Table 6 contains Status A density losses that are observed from processed strips when they are exposed to 50 klux intensity light for 28 days. Fade values from the indicated intitial densities of 1.7 and 1.0 are listed as decreases in density.

TABLE 6

| Stabilizer | Fade from 1.70 | Fade from 1.00 |
| --- | --- | --- |
| Comparison (SC-2) | −.68 | −.40 |
| Invention 1 (S-5) | −.56 | −.37 |
| Invention 2 (S-9) | −.58 | −.37 |

Additional elements were also prepared as listed in Table 7 below, to obtain the levels of stabilizer indicated in millimoles per square foot (mm/ft²). Coupler level in all elements was 50 mg/ft² while solvent levels were related to coupler levels in accordance with the Formulation A solvent/coupler ratios of Table 3 for Elements 1–4 of Table 7, and Formulation C ratios for Element 6–8. Element 5 could not be coated at an equivalent level of elements 6–8 as Formulation C crystallized (see Table 4). The elements were otherwise prepared, exposed and processed as in Example 2. In each case the test was done by irradiating the sample with a light from a high intensity Xenon light source. Table 7 below contains Status A density losses that are observed from processed strips when they are exposed to 50 klux intensity light for 28 days. Fade values from the indicated intitial densities of 1.70, 1.00 and 0.50 are listed in Table 7 as decreases in density.

TABLE 7

| ELEMENT | STABILIZER | | LEVEL (mm/ft²) | DENSITY LOSS, 1.70 | DENSITY LOSS, 1.00 | DENSITY LOSS, .05 |
| --- | --- | --- | --- | --- | --- | --- |
| 1 | SC-3 | (C) | 0.058 | −0.61 | −0.45 | −0.32 |
| 2 | S-9 | (I) | 0.049 | −0.69 | −0.46 | −0.29 |
| 3 | S-5 | (I) | 0.049 | −0.71 | −0.51 | −0.31 |
| 4 | S-13 | (I) | 0.049 | −0.57 | −0.41 | −0.28 |
| 5 | SC-3 | (C) | —* | — | — | — |
| 6 | S-9 | (I) | 0.170 | −0.52 | −0.35 | −0.25 |
| 7 | S-5 | (I) | 0.170 | −0.47 | −0.33 | −0.26 |
| 8 | S-13 | (I) | 0.170 | −0.44 | −0.31 | −0.24 |

(I) = Invention
(C) = Comparison
* = Formulation C crystallized and therefore was not coated at an equivalent level as Elements 6–8 (see text).

The invention has been described in detail with particular reference to preferred embodiments thereof, but it will be understood that variations and modifications can be effected within the spirit and scope of the invention.

What is claimed is:

1. A photographic element comprising a silver halide emulsion layer having associated therewith, a dye-forming coupler and a dye stabilizer which has a melting point of less than 100° C. and is of the formula:

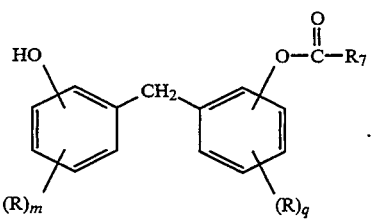

wherein:
  each R independently represents an alkyl, alkenyl, cycloalkyl or aryl group, or in combination with the benzene ring to which it is attached represents the atoms necessary to complete a fused ring system, any of which may be substituted or unsubstituted;
  m and q independently represent an integer of 0 to 3;
  in which $R^7$ represents a substituted or unsubstituted aliphatic or aromatic group.

2. A photographic element according to claim 1 wherein the coupler is a yellow dye-forming coupler of the formula (E):

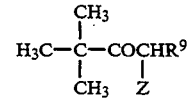

wherein:
  R9 represents a substituted or unsubstituted N-phenylcarbamoyl group;
  Z represents a hydrogen atom or a group releasable upon coupling with an oxidized product of a developing agent; and
  $R^9$ and Z may form a dimer or a higher polymer.

3. A photographic element according to claim 2 wherein $R^7$ represents a substituted or unsubstituted aliphatic group of more than 1 C atom.

4. A photographic element according to claim 2 wherein the stabilizer is of the formula:

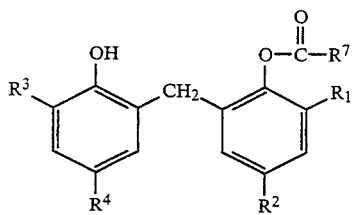

(D)

5. A photographic element according to claim 4 wherein each of $R^1$, $R^2$, $R^3$ and $R^4$ are substituted or unsubstituted alkyl.

6. A photographic element according to claim 4 wherein $R^1$ and $R^3$ are each a t-butyl, and $R^2$ and $R^4$ are each a methyl or t-butyl.

7. A photographic element according to claim 4 wherein $R^7$ has more than 4 C atoms.

8. A photographic element according to claim 1 in which $R^1$ and $R^3$ are the same, and $R^2$ and $R^4$ are the same.

9. A photographic element according to claim 1 wherein $R^7$ represents a substituted or unsubstituted aliphatic group of more than 1 C atom.

10. A photographic element according to claim 1 wherein the stabilizer is of the formula:

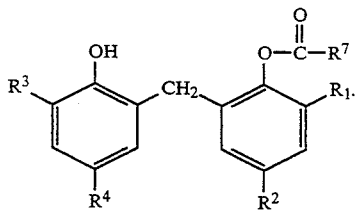

(C)

11. A photographic element according to claim 10 wherein $R^1$ and $R^3$ are each t-butyl, and $R^2$ and $R^4$ are each methyl.

12. A photographic element comprising a silver halide emulsion layer having associated therewith, a dye-forming coupler of formula (F) and a dye stabilizer of formula (D) and which stabilizer has a melting point of less than 100° C.:

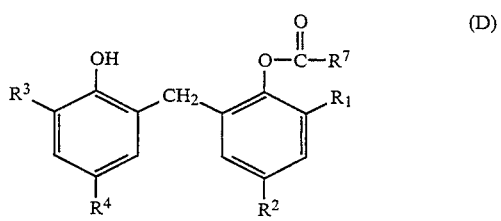

wherein:
each of $R^1$, $R^2$, $R^3$ and $R^4$ independently represents an alkyl, alkenyl, cycloalkyl or aryl group, any of which may be substituted or unsubstituted;
$R^7$ represents a substituted or unsubstituted aliphatic or aromatic group;

wherein:
$R^{10}$ is a substituted or unsubstituted alkyl group of 1 to 4 carbon atoms;
W is CO, $PO_3$ or $SO_2$;
Z is a substituted or unsubstituted aryloxy group releasable upon coupling with an oxidized product of a developing agent;
v is 1 or, when W is $PO_3$ v is 2;
Ballast is a ballast group which renders the coupler nondiffusible in the element.

13. A photographic element according to claim 12 wherein $R^7$ represents a substituted or unsubstituted aliphatic group.

14. A photographic element according to claim 10 wherein $R^1$ and $R^3$ are each t-butyl, and $R^2$ and $R^4$ are each methyl.

* * * * *

UNITED STATES PATENT AND TRADEMARK OFFICE
CERTIFICATE OF CORRECTION

PATENT NO. : 5,426,021
DATED : June 20, 1995
INVENTOR(S) : S. Krishnamurthy et al.

It is certified that error appears in the above-indentified patent and that said Letters Patent is hereby corrected as shown below:

On the title page insert the following:

--[73] Assignee: Eastman Kodak Company, Rochester, N.Y.--.

Insert the Following Primary Examiner to read
--Attorney, Agent, or Firm - Gordon M. Stewart--.

Signed and Sealed this

Thirty-first Day of October 1995

*Attest:*

BRUCE LEHMAN

*Attesting Officer*      *Commissioner of Patents and Trademarks*